(12) United States Patent
Yu (10) Patent No.: US 11,058,746 B2
(45) Date of Patent: *Jul. 13, 2021

(54) **USE OF IMMUNOMODULATORY PROTEIN FROM *GANODERMA* IN INHIBITING FIBROSIS**

(71) Applicant: MYCOMAGIC BIOTECHNOLOGY CO., LTD, New Taipei (TW)

(72) Inventor: Cheng-Chia Yu, Taichung (TW)

(73) Assignee: MYCOMAGIC BIOTECHNOLOGY CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/714,218

(22) Filed: Sep. 25, 2017

(65) Prior Publication Data

US 2019/0091286 A1 Mar. 28, 2019

(51) Int. Cl.
*A61K 38/16* (2006.01)

(52) U.S. Cl.
CPC .................................. *A61K 38/168* (2013.01)

(58) Field of Classification Search
None
See application file for complete search history.

(56) References Cited

U.S. PATENT DOCUMENTS

| 9,937,226 B2 * | 4/2018 | Yu | A61K 38/16 |
| 2011/0318429 A1 * | 12/2011 | Ko | A61K 31/517 424/649 |
| 2013/0296253 A1 * | 11/2013 | Ko | A61K 38/168 514/19.8 |
| 2014/0079737 A1 * | 3/2014 | Ou | A61K 38/16 424/278.1 |
| 2014/0086946 A1 * | 3/2014 | Ko | A61K 31/282 424/185.1 |
| 2016/0115208 A1 * | 4/2016 | Chao | A61K 38/168 514/17.8 |
| 2016/0184389 A1 * | 6/2016 | Yu | A61K 38/16 424/185.1 |
| 2017/0080048 A1 * | 3/2017 | Hsu | A61K 38/16 |
| 2017/0173110 A1 * | 6/2017 | Ko | A61K 31/337 |
| 2017/0368119 A1 * | 12/2017 | Wu | A61K 38/168 |

OTHER PUBLICATIONS

Lee et al. "Inhibitory effect of GMI, an immunomodulatory protein from Ganoderma Microsporum, on myofibroblast activity and proinflammatory cytokines in human fibrotic buccal mucosal fibroblasts" Environmental Toxicology 33:32-40 (Year: 2017).*
Cox and Erler "Fibrosis, cancer and the premetastatic niche" Breast Cancer Management 3:453-455. (Year: 2014).*
Wynn, TA, Cellular and Molecular Mechanisms of Fibrosis, J Pathol, Jan. 2008; 214(2): 199-210. doi:10.1002/path.2277.

* cited by examiner

*Primary Examiner* — Sudhakar Katakam
*Assistant Examiner* — Zachary J Miknis
(74) *Attorney, Agent, or Firm* — WPAT, P.C., Intellectual Property Attorneys; Anthony King (57) ABSTRACT

The present invention provides a method of preventing or treating fibrosis in a subject, comprising administering an effective amount of an immunomodulatory protein derived from *Ganoderma lucidum, Ganoderma lucidum, Ganoderma tsugae, Ganoderma microsporum* or *Ganoderma sinensis* to the subject, thereby preventing or treating a fibrosis.

3 Claims, 10 Drawing Sheets

Specification includes a Sequence Listing.

USE OF IMMUNOMODULATORY PROTEIN FROM *GANODERMA* IN INHIBITING FIBROSIS

FIELD OF THE INVENTION

The present invention relates to the field of fibrosis disease. Particularly, the present invention use of use of an immunomodulatory protein from *Ganoderma microsporum* in inhibition, prevention and/or treatment of a fibrosis.

BACKGROUND OF THE INVENTION

Progressive fibrosis is characterized by the excessive production and accumulation of extracellular matrix (ECM) components, including fibrillar collagens (collagen I and III) or collagen IV, which is one of the major components of the basement membrane and glycoproteins (e.g. fibronectin) and proteoglycans (e.g. heparin sulphate) as well. The ECM is a functional tissue whose components possess not only scaffolding characteristics, but also growth facilitating, mitogenic, and other bioactive properties. Progressive fibrosis occurs when tissue remodeling is shifted towards excessive deposition of ECM leading to destruction of the original tissue architecture and to gradual decline of tissue and/or organ function. Progressive fibrosis is a pathological process leading to the formation of permanent scar tissue; in several cases it causes organ failure and might lead to death.

Persistent activation of myofibroblasts attributes to excessive deposition of ECM. The increased activity of myofibroblast has been found in multiple tissue fibroses, including heart, lung and oral submucous fibrosis (OSF). OSF is a chronic, debilitating disease of the oral cavity characterized by progressive fibrosis of the submucosal tissues (lamina propria and deeper connective tissues). Although the exact pathological mechanism has not been well-established, there are several possible causes for the abnormal fibrosis. It has been indicated that OSF is associated with *areca* quid chewing habit. The fibrosis results in restriction of mouth opening and involves the palates, tonsillar fossa, buccal mucosa and underlying muscle.

There is no generally accepted therapy at present for progressive fibrosis in fibroproliferative disorders, particularly OSF.

SUMMARY OF THE INVENTION

The invention surprisingly found that an immunomodulatory protein from *Ganoderma* can decrease myofibroblast activity in fibrotic buccal mucosal fibroblast by inhibiting collagen gel contraction, migration and invasion. The immunomodulatory protein also can decrease the expression level of interleukin (IL)-6 and IL-8. Therefore, the immunomodulatory protein can be used as an anti-fibrosis agent to prevent or treat fibrosis.

The present invention provides a method of preventing or treating fibrosis in a subject, comprising administering an effective amount of an immunomodulatory protein derived from *Ganoderma lucidum*, *Ganoderma lucidum*, *Ganoderma tsugae*, *Ganoderma microsporum* or *Ganoderma sinensis* to the subject, thereby preventing or treating a fibrosis.

The present invention also provides a method of decreasing myofibroblast activity in a cell or a subject, comprising contacting or administering an immunomodulatory protein derived from *Ganoderma lucidum*, *Ganoderma lucidum*, *Ganoderma tsugae*, *Ganoderma microsporum* or *Ganoderma sinensis* to the subject.

Particular embodiments of the fibrosis include cardiac fibrosis, scleroderma, skeletal muscle fibrosis, hepatic fibrosis, kidney fibrosis, pulmonary fibrosis, diabetic fibrosis and OSL.

Particular embodiments of the immunomodulatory protein include LZ-8 derived from *Ganoderma lucidum*, FIP-gts derived from *Ganoderma tsugae*, GMI derived from *Ganoderma microsporum*, or FIP-gja derived from *Ganoderma sinensis*.

Further embodiments of the immunomodulatory protein include that has an amino acid sequence as shown in SEQ ID NO: 1 or SEQ ID NO: 2.

In some embodiments, the myofibroblast activity is decreased by inhibiting collagen gel contraction, migration, invasion and wound healing abilities. In another embodiment, the method decreases the expression level of interleukin (IL)-6 and IL-8.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

In this application, the use of the singular includes the plural, the article "a" or "an" means "at least one", and the use of "or" means "and/or", unless specifically stated otherwise.

In this application, the word "comprise," or variations such as "comprises" or "comprising," indicate the inclusion of any recited integer or group of integers but not the exclusion of any other integer or group of integers in the specified method, structure, or composition.

As used herein, "inhibit," "prevent" or "reduce," or "inhibiting," "preventing" or "reducing" are used interchangeably herein. These terms refer to the decrease in a measured parameter in a treated cell (tissue or subject) in comparison to an untreated cell (tissue or subject). A comparison can also be made of the same cell or tissue or subject between before and after treatment. The decrease is sufficient to be detectable.

As used herein, "treatment" or "treating" or "ameliorating" are used interchangeably herein. These terms refer to an approach for obtaining beneficial or desired results including, but not limited to, therapeutic benefit and/or a prophylactic benefit. Therapeutic benefit pertains to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. Those in need of treatment include those already with the condition or disorder as well as those prone to have the condition or disorder or those in which the condition or disorder is to be prevented.

As used herein, "therapeutically effective amount" means an amount sufficient to treat a subject afflicted with a disease or to alleviate a symptom or a complication associated with the disease.

As used herein, "subject" refers to either a human or non-human animal.

In one aspect, the invention provides a method of preventing or treating fibrosis in a subject, comprising administering an effective amount of an immunomodulatory protein derived from *Ganoderma lucidum, Ganoderma lucidum, Ganoderma tsugae, Ganoderma microsporum* or *Ganoderma sinensis* to the subject, thereby preventing or treating a fibrosis.

In one embodiment, the fibrosis is selected from cardiac fibrosis, scleroderma, skeletal muscle fibrosis, hepatic fibrosis, kidney fibrosis, pulmonary fibrosis, diabetic fibrosis or OSL. In a further aspect, the fibrosis is OSL.

In some embodiments, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis*. In further embodiment, the immunomodulatory protein has an amino acid sequence as shown in SEQ ID NO: 1 or SEQ ID NO: 2.

The sequences of SEQ ID NO:1 (i.e., GMI described herein) and SEQ ID NO: 2 are listed as follows.

```
                                                (SEQ ID NO: 1)
MSDTALIFTLAWNVKQLAFDYTPNWGRGRPSSFIDTVTFPTVLTDKAYTY
RVVVSGKDLGVRPSYAVESDGSQKINFLEYNSGYGIADTNTIQVYVIDPD
TGNNFIVAQWN (SEQ ID NO: 2)
EAEAEFMSDTALIFTLAWNVKQLAFDYTPNWGRGRPSSFIDTVTFPTVLT
DKAYTYRVVVSGKDLGVRPSYAVESDGSQKINFLEYNSGYGIADTNTIQV
YVIDPDTGNNFIVAQWNYLEQKLISEEDLNSAVDHHHHHH
```

In one embodiment, the method decreases myofibroblast activity by inhibiting collagen gel contraction, migration, invasion and wound healing abilities. In another embodiment, the method decreases the expression level of interleukin (IL)-6 and IL-8.

Accordingly, the present invention provides a method of decreasing myofibroblast activity in a cell or a subject, comprising contacting or administering an immunomodulatory protein derived from *Ganoderma lucidum, Ganoderma lucidum, Ganoderma tsugae, Ganoderma microsporum* or *Ganoderma sinensis* to the subject. In some embodiments, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis*. In further embodiment, the immunomodulatory protein has an amino acid sequence as shown in SEQ ID NO: 1 or SEQ ID NO: 2.

In one embodiment, the myofibroblast activity is decreased by inhibiting collagen gel contraction, migration, invasion and wound healing abilities. In another embodiment, the method decreases the expression level of interleukin (IL)-6 and IL-8.

In one embodiment, the effective amount used in the methods of the present invention ranges from about 25 mg to about 55 mg of the immunomodulatory protein per kg body weight. In some embodiments, the effective amount ranges from about 25 mg to about 50 mg, about 25 mg to about 45 mg, about 25 mg to about 40 mg, about 25 mg to about 35 mg, about 25 mg to about 30 mg, about 30 mg to about 55 mg, about 32 mg to about 55 mg, about 34 mg to about 55 mg, about 36 mg to about 55 mg, about 38 mg to about 55 mg, about 40 mg to about 55 mg, about 30 mg to about 50 mg, about 32 mg to about 50 mg, about 34 mg to about 50 mg, about 36 mg to about 50 mg, about 38 mg to about 50 mg, about 40 mg to about 50 mg, about 30 mg to about 45 mg, about 32 mg to about 45 mg, about 34 mg to about 45 mg, about 45 mg, about 36 mg to about 45 mg, about 38 mg to about 45 mg, about 40 mg to about 45 mg, about 30 mg to about 40 mg, about 32 mg to about 40 mg, about 34 mg to about 40 mg or about 36 mg to about 40 mg per kg body weight. In a further embodiment, the effective amount ranges from about 36 mg to about 40 mg per kg body weight.

The immunomodulatory protein or a recombination thereof of the invention can be administered to a patient either alone or in pharmaceutical compositions where it is mixed with suitable carriers and excipients. The immunomodulatory protein or a recombination thereof or a composition of the invention can be administered parenterally, such as by intravenous injection or infusion, intraperitoneal injection, subcutaneous injection, or intramuscular injection. The immunomodulatory protein or a recombination thereof or a composition can be administered orally or through appropriate formulation with carriers and excipients to form tablets, pills, capsules, liquids, gels, syrups, slurries, suspensions and the like. The immunomodulatory protein or a recombination thereof or a composition can be administered topically, such as by skin patch. The immunomodulatory protein or a recombination thereof or a composition can be formulated into topical creams, skin or mucosal patch, liquids or gels suitable to topical application to mucosal membrane surfaces.

The dosage of the immunomodulatory protein or a recombination thereof or a composition suitable for use according to the present invention can be determined by those skilled in the art on the basis of the disclosure herein. The medicament will contain an effective dosage (depending upon the route of administration and pharmacokinetics of the active agent) of Suitable pharmaceutical carriers and excipients are suitable for the particular route of administration of the formulation (i.e., oral, parenteral, topical or by inhalation). The immunomodulatory protein or a recombination thereof is mixed into the pharmaceutical composition by means of mixing, dissolving, granulating, dragee-making, emulsifying, encapsulating, entrapping or lyophilizing processes. The pharmaceutical compositions for parenteral administration include aqueous solutions of the immunomodulatory protein or a recombination thereof in water-soluble form. Additionally, suspensions of the immunomodulatory protein or a recombination thereof may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

Without further elaboration, it is believed that one skilled in the art can utilize the present invention to its fullest extent on the basis of the preceding description. The following examples are, therefore, to be construed as merely illustrative and not a limitation of the scope of the present invention in any way.

EXAMPLES

GMI Protein

GMI, manufactured by Mycomagic Biotechnology Co., Ltd. (Taipei, Taiwan), was generated and ameliorated from *Ganoderma microsporum*. The GMI is prepared according to the method described in U.S. Pat. Nos. 7,601,808 and 7,601,808.

OSF Tissues Acquirement and Cell Culture

Fibrotic BMFs (fBMFs) were isolated from OSF patients recruited in the Oral Medicine Center (Chung Shan Medical University Hospital, Taichung, Taiwan) with informed consent and the protocol was approved by Institutional Review Board of Chung Shan Medical University Hospital. Fibroblasts derived from normal buccal mucosa (BMFs) and fBMFs were cultured according to the criteria and methods known in the art. Cell cultures between the third and eighth passages were used in this study.

MTT Assay

For determination of the cytotoxic effect of GMI in fBMFs and BMFs, cells were seeded at $1\times10^5$ cells/500 gl/well in 24-well plates in the presence of different concentration of GMI or vehicle at 37° C. for 48 hours followed by MTT (3-(4,5-dimethylthiazol-2-yl)-2,5-diphenyl tetrazolium bromide) treatment. The blue formazan crystals of viable cells were dissolved in DMSO and then evaluated spectrophotometrically at 570 nm. DMSO-treated group was set as 100%, and data were presented as percentage of DMSO control. IC50 values were calculated by GraFit software (Erithacus Software Ltd., West Sussex, UK).

Collagen Gel Contraction Assay

The bioactivity of myofibroblast function was performed by collagen contraction assay (Sigma-Aldrich Chemical Co., St. Louis, Mo., USA). $2\times10^5$ cells were suspended in cold collagen solution (2 mg/ml) and cell-collagen mixtures were then loaded into 24-well plates at 0.5 ml/well and covered with 1 ml of culture medium after polymerization of collagen. To initiate contraction, collagen gels were gently dissociated from the sides of the culture dishes with a sterile spatula. The diameter changes of collagen gel size (contraction index) were recorded at various times and quantified by ImageJ software.

Wound Healing Assay

Cells were seeded into 6-well culture dishes. Wounds were introduced to the confluent monolayer of cells with a sterile 200 pL plastic pipette tip to create a denuded area. Cell movement toward the center of the wound area was photographed at 0 and 48 hours under a microscope.

Quantitative Real-Time PCR (qRT-PCR)

Total RNA was extracted from cells using Trizol reagent according to the manufacturer's protocol (Invitrogen Life Technologies, Carlsbad, Calif., USA). qRT-PCRs of mRNAs were reverse-transcribed using the Superscript III first-strand synthesis system for RT-PCR (Invitrogen Life Technologies, Carlsbad, Calif., USA). qRT-PCR reactions on resulting cDNAs were performed on an ABI StepOne™ Real-Time PCR Systems (Applied Biosystems).

Western Blot Analysis

Western blot analysis was conducted as previously described (Yang P Y et al. 2017). The primary antibodies against COL1A1, α-SMA, FN1 and vimentin were purchased from Santa Cruz Biotechnology, Inc. (Santa Cruz, Calif., USA). Following primary antibodies, the membranes were incubated with corresponding secondary antibodies. The immunoreactive bands were developed using an ECL-plus chemiluminescence substrate (Perkin-Elmer, Waltham, Mass., USA) and captured by LAS-1000 plus Luminescent Image Analyzer (GE Healthcare, Piscataway, N.J., USA).

Enzyme-Linked Immunosorbent Analysis (ELISA)

For detection of IL-6 and IL-8, fBMFs were cultured in 6-well plates with various concentration of GMI for 48 hours. Cell supernatants were collected and centrifuged to remove dead cells. The supernatants were then analyzed by ELISA using IL-6 or IL-8 specific kits from eBioscience according to the manufacturer's protocol.

Statistical Analysis

SPSS Statistics version 13.0 was used for statistical analysis. Student's t test or ANOVA analysis were used to determine statistical significance of the differences among experimental groups; p values less than 0.05 were considered statistically significant.

Figure 1:
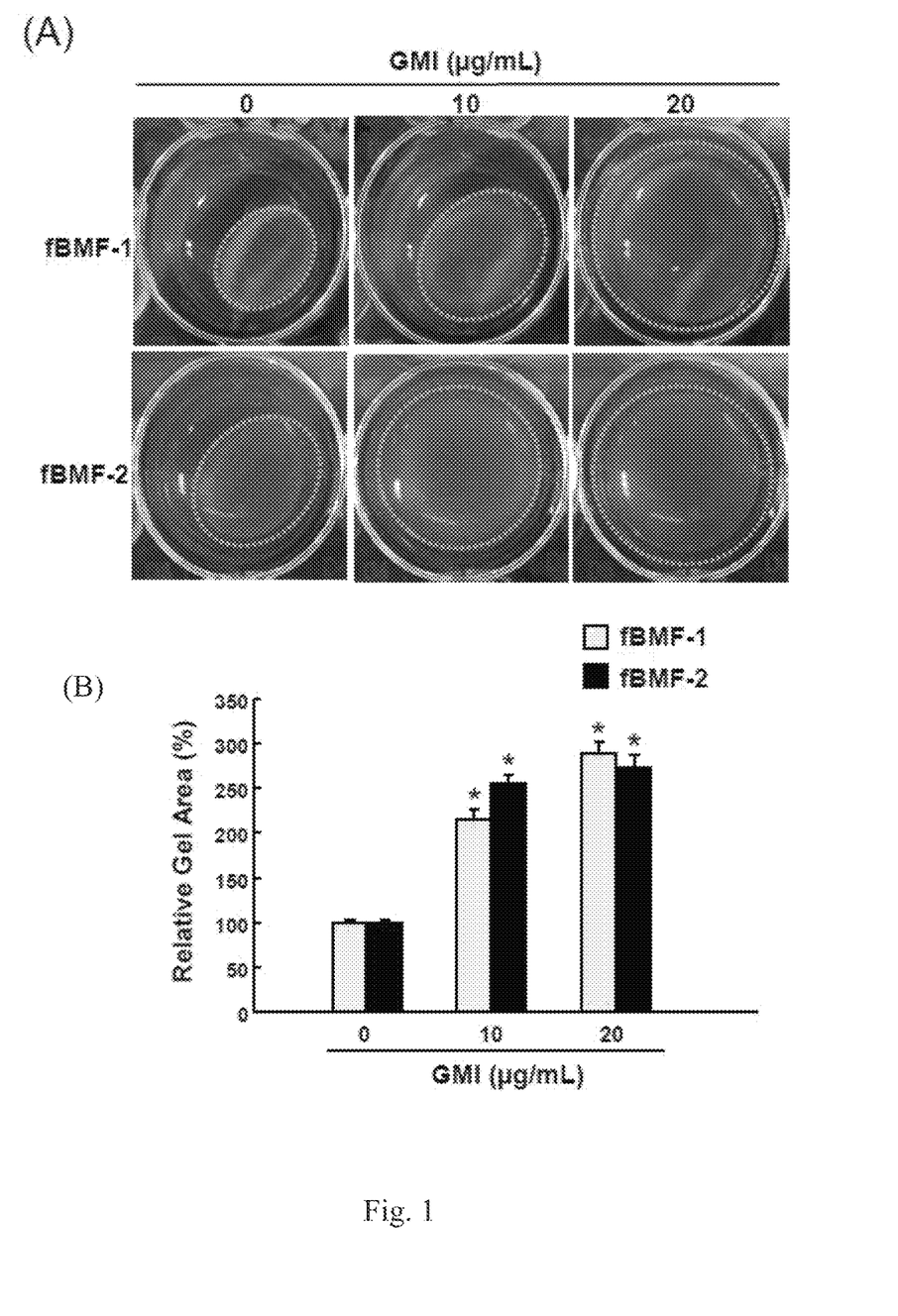
FIG. 1 shows that GMI inhibits contraction and wound-healing activity of fBMF. (A) Different concentration GMI-treated fBMF were subjected to collagen gel contraction assay (three replicates for each concentration). Images of gels gel areas (dotted circles) were calculated by ImageJ software. The experiments were repeated for three times and data from a representative experiment were presented. *, $p<0.05$ as comparison with non-GMI treated group. (B) Single cell suspension of fBMF treated with GMI was analyzed by wound healing assay.

Example 1 GMI Reduces the Collagen Contractile and Wound Healing Abilities of fBMFs Myofibroblasts are specialized contractile cells and responsible for wound closure. We found that GMI-treated fBMFs displayed a significant reduction of cell contraction capability at 10 µg/ml and 20 µg/ml (FIG. 1A). Moreover, the wound healing ability was markedly inhibited at both concentrations as compared to fBMFs cells without GMI treatment (FIG. 1B), indicating that GMI possess the potential to impede the cell migration of myofibroblasts.

Example 2 GMI Downregulates the Migration and Invasion Abilities of fBMFs

Figure 2:
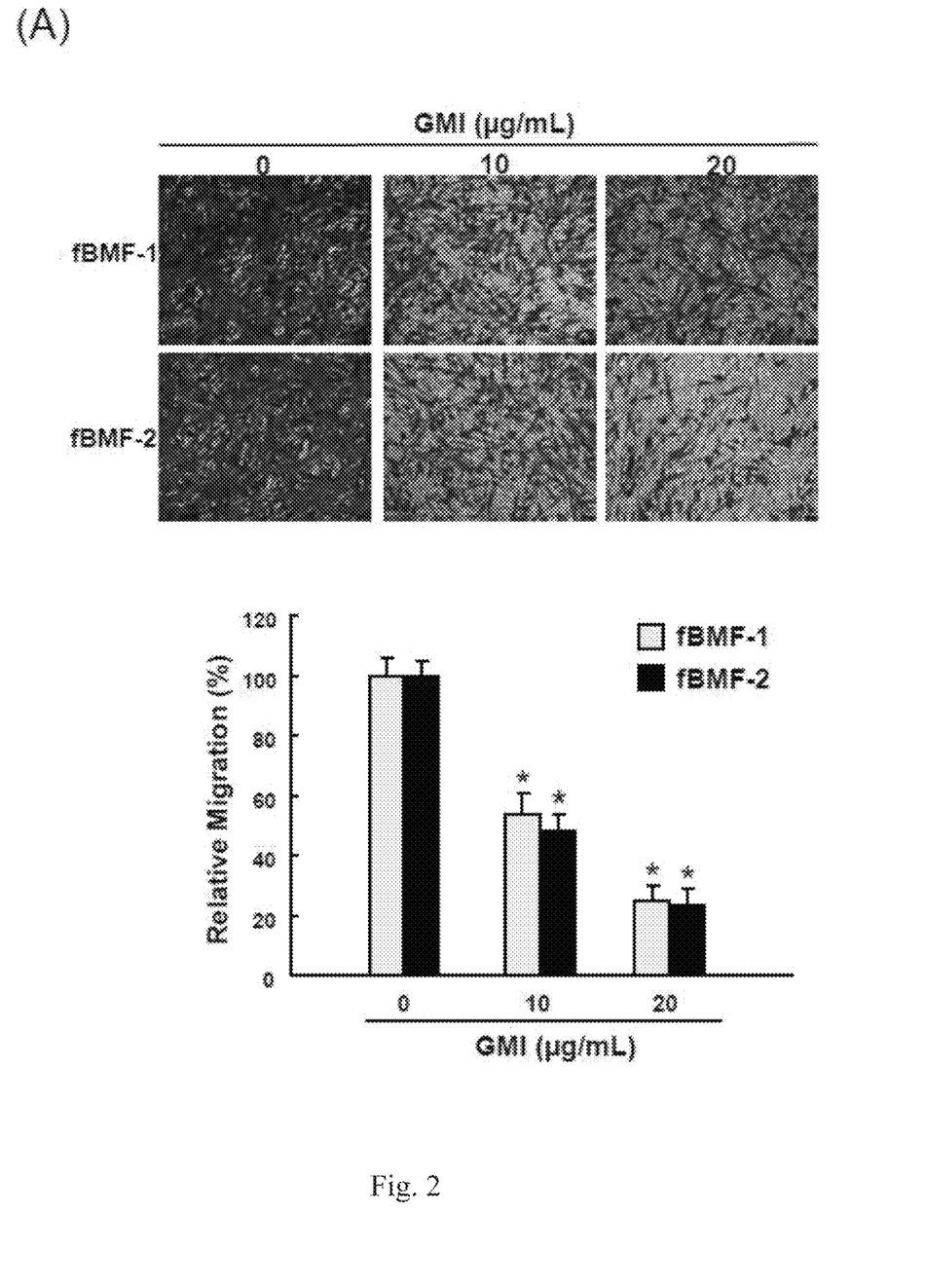
FIG. 2 shows that GMI represses migration and invasion activity in of fBMF. Different concentration GMI-treated fBMF were subjected to migration assay (A) and matrix invasion assay (B). The experiments were repeated three times and representative results were shown. Results are means±SD. *, $p<0.05$ vs. Control.

To further evaluate the influence of GMI on the activated myofibroblast properties, fBMFs were treated with various concentration of GMI and cell migration and invasion abilities were examined using transwell system. As shown in FIG. 2A, we observed a dose-dependent effect of GMI on the migration capacity. Besides, our result demonstrated that invasion of myofibroblasts was reduced by 70% in the presence of 20 μg/ml GMI (FIG. 2B). In associated with the results from migration assay, we showed that GMI exhibited a significant anti-invasion capacity in myofibroblasts.

Figure 3:
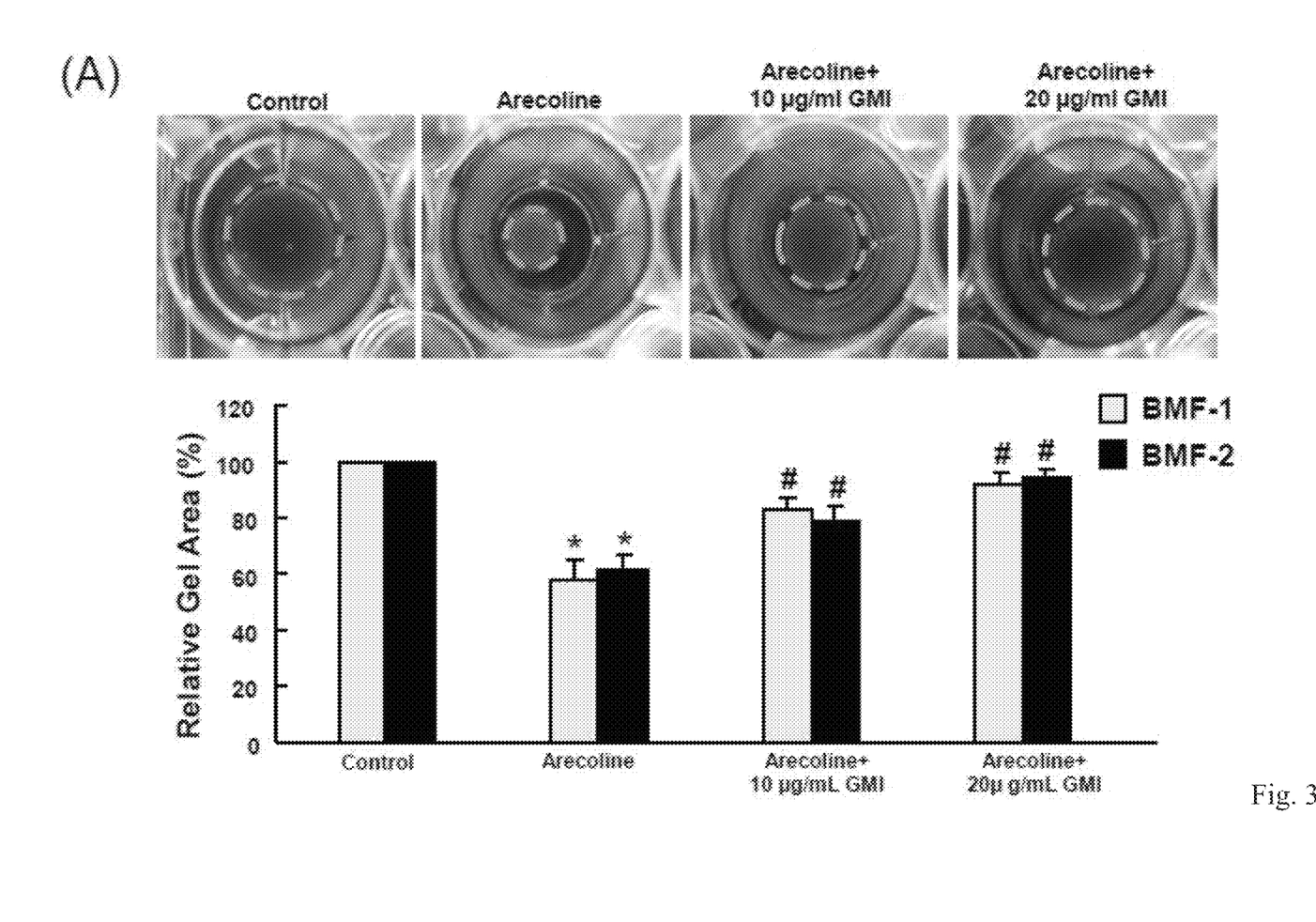
FIG. 3 shows that GMI suppresses arecoline-induced collagen contraction and wound-healing capabilities of BMF. Single cell suspension of arecoline-treated BMF with GMI treatment was analyzed by collagen gel contraction assay (A) and wound healing assay (B). *$P<0.05$ arecoline group versus control group; #$P<0.05$ GMI+arecoline versus+arecoline group.
Figure 4:
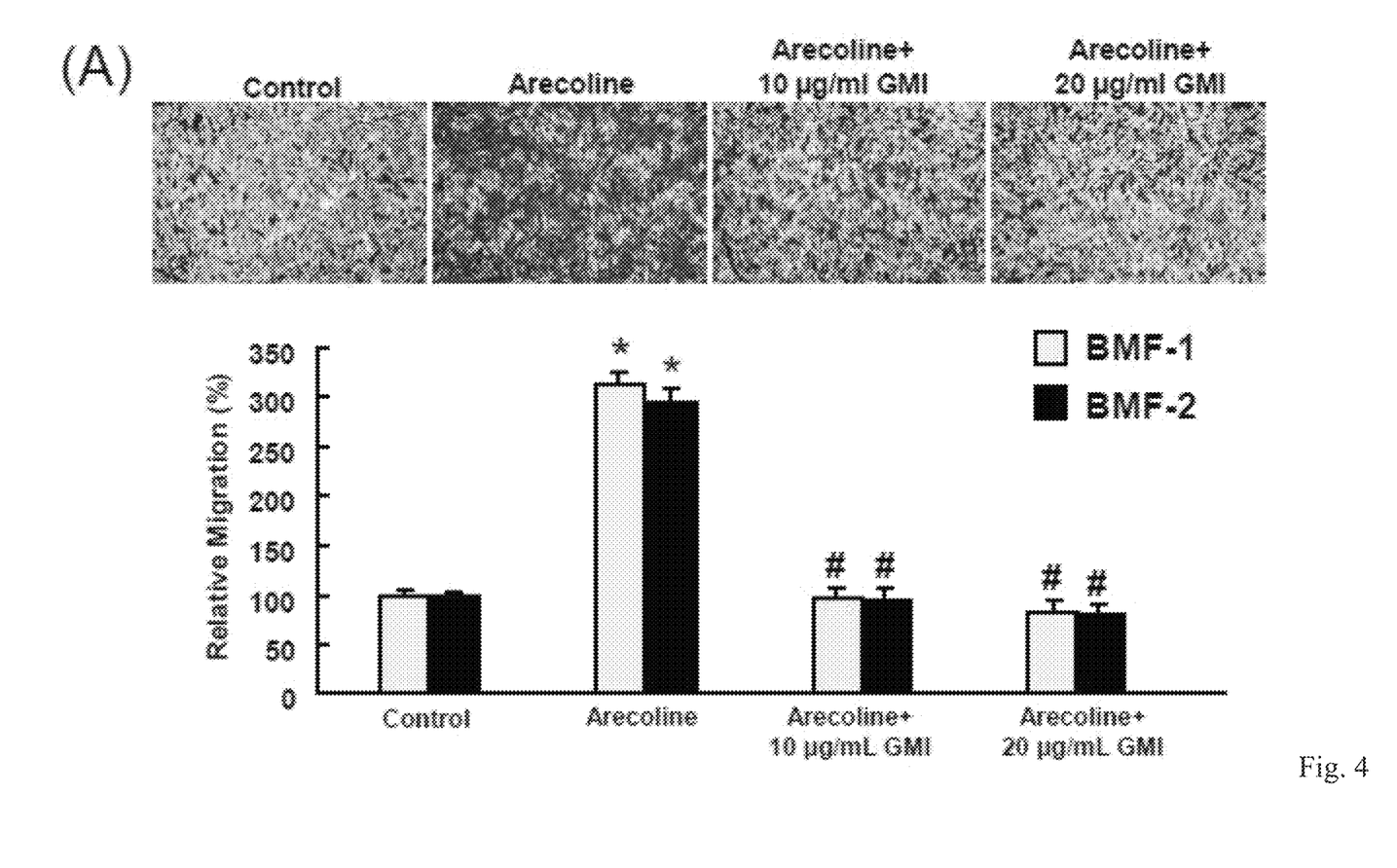
FIG. 4 shows that GMI represses arecoline-induced myofibroblastic differentiation activity. Single cell suspension of arecoline-treated BMF with GMI treatment was analyzed by migration assay (A) and matrix invasion assay (B). *$P<0.05$ arecoline group versus control group; #$P<0.05$ GMI+arecoline versus+arecoline group.

Example 3 GMI Suppresses the Myofibroblast Activities in Arecoline-Stimulated BMFs Our previous studies have demonstrated that arecoline, an alkaloid found in the *areca* nut, could induce myofibroblast transdifferentiation in BMFs, therefore, we sought to verify our findings using the arecoline-treated BMFs in the following tests. As expected, arecoline treatment induced the collagen contraction ability of BMFs whereas application of GMI significantly reversed this phenomenon (FIG. 3A). Also, GMI decreased the wound healing ability induced by arecoline in a dose-dependent fashion (FIG. 4B). In addition, the increased migration capacity was significantly blocked by GMI treatment (FIG. 4A). And the invasive phenotype of BMFs after arecoline stimulation was also inhibited by GMI (FIG. 4B).

Figure 5:
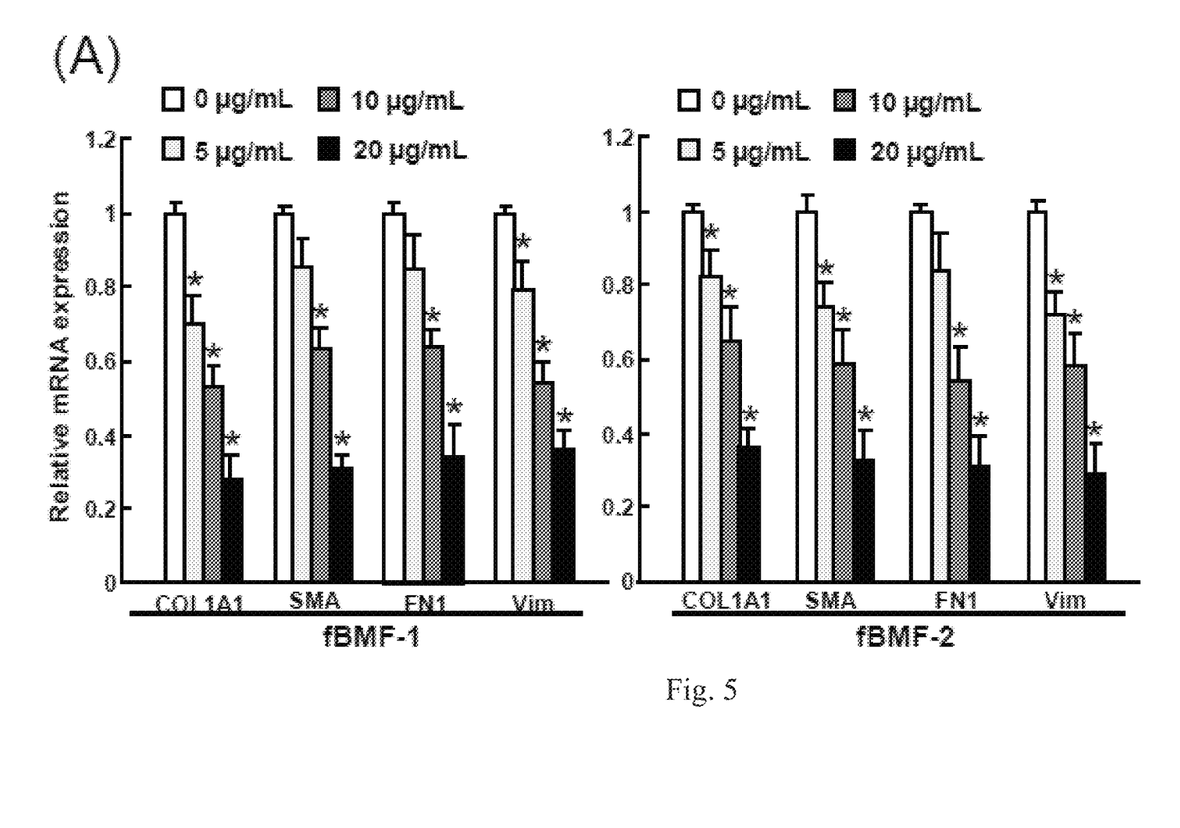
FIG. 5 shows that GMI treatment suppresses myofibroblasts marker expression and pro-inflammatory cytokines in fBMF. The indicated myofibroblasts marker expression levels (COL1A1, α-SMA, fibronectin, and vimentin) in the GMI-treated fBMF were analyzed by quantitative real-time PCR (A) and western blotting (B). The experiments were repeated three times and representative results were shown. The secreted protein expression levels of IL-6 (C) and IL-8 (D) in GMI-treated fBMF were analyzed by western blot. Results are means±SD. *, $p<0.05$ vs. Control.

Example 4 GMI Reduces the Myofibroblasts Marker Expression and Pro-Inflammatory Cytokines in fBMFs To investigate the possible mechanisms underlying the anti-fibrotic effect of GMI, we assessed the expression of fibrogenic markers in fBMFs. As shown in FIG. 5A, GMI significantly downregulated the mRNA expression of type I collagen (COL1A1), α-SMA, fibronectin (FN), and vimentin in these fBMFs in a dose-dependent manner. In consistent with the gene expression, the protein level of COL1A1, α-SMA, FN and vimentin were also dose-dependently downregulated in fBMFs (FIG. 5B). Furthermore, we examined the expression of pro-inflammatory cytokines in these fBMFs since GMI was found to exhibit anti-inflammatory effect. And our results showed that there was a dose-dependent suppression of IL-6 or IL-8 following exposure of GMI (FIGS. 5C and D).

What is claimed is:

1. A method of decreasing myofibroblast activity in a subject in need of treatment for oral submucous fibrosis (OSF), comprising administering an immunomodulatory protein derived from *Ganoderma microsporum* to the subject;
    wherein the immunomodulatory protein has the amino acid sequence of SEQ ID NO: 1.

2. The method of claim 1, wherein myofibroblast activity in the subject is decreased by inhibiting collagen gel contraction, migration, invasion and wound healing abilities.

3. The method of claim 1, wherein the expression level of interleukin (IL)-6 and IL-8 in the subject is decreased.

* * * * *

SEQUENCE LISTING

```
<160> NUMBER OF SEQ ID NOS: 2

<210> SEQ ID NO 1
<211> LENGTH: 111
<212> TYPE: PRT
<213> ORGANISM: Ganoderma microsporum

<400> SEQUENCE: 1

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
            20                  25                  30

Phe Ile Asp Thr Val Thr Phe Pro Thr Val Leu Thr Asp Lys Ala Tyr
        35                  40                  45

Thr Tyr Arg Val Val Val Ser Gly Lys Asp Leu Gly Val Arg Pro Ser
    50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
            100                 105                 110

<210> SEQ ID NO 2
<211> LENGTH: 140
<212> TYPE: PRT
<213> ORGANISM: artificial sequence
<220> FEATURE:
<223> OTHER INFORMATION: synthetic polypeptide

<400> SEQUENCE: 2

Glu Ala Glu Ala Glu Phe Met Ser Asp Thr Ala Leu Ile Phe Thr Leu
1               5                   10                  15

Ala Trp Asn Val Lys Gln Leu Ala Phe Asp Tyr Thr Pro Asn Trp Gly
            20                  25                  30

Arg Gly Arg Pro Ser Ser Phe Ile Asp Thr Val Thr Phe Pro Thr Val
        35                  40                  45

Leu Thr Asp Lys Ala Tyr Thr Tyr Arg Val Val Val Ser Gly Lys Asp
```

-continued

```
            50                  55                  60
Leu Gly Val Arg Pro Ser Tyr Ala Val Glu Ser Asp Gly Ser Gln Lys
65                  70                  75                  80

Ile Asn Phe Leu Glu Tyr Asn Ser Gly Tyr Gly Ile Ala Asp Thr Asn
                85                  90                  95

Thr Ile Gln Val Tyr Val Ile Asp Pro Asp Thr Gly Asn Asn Phe Ile
                100                 105                 110

Val Ala Gln Trp Asn Tyr Leu Glu Gln Lys Leu Ile Ser Glu Glu Asp
            115                 120                 125

Leu Asn Ser Ala Val Asp His His His His His His
            130                 135                 140
```